Feb. 4, 1964 A. MEILLAND Plant Pat. 2,359
ROSE PLANT
Filed Feb. 5, 1963
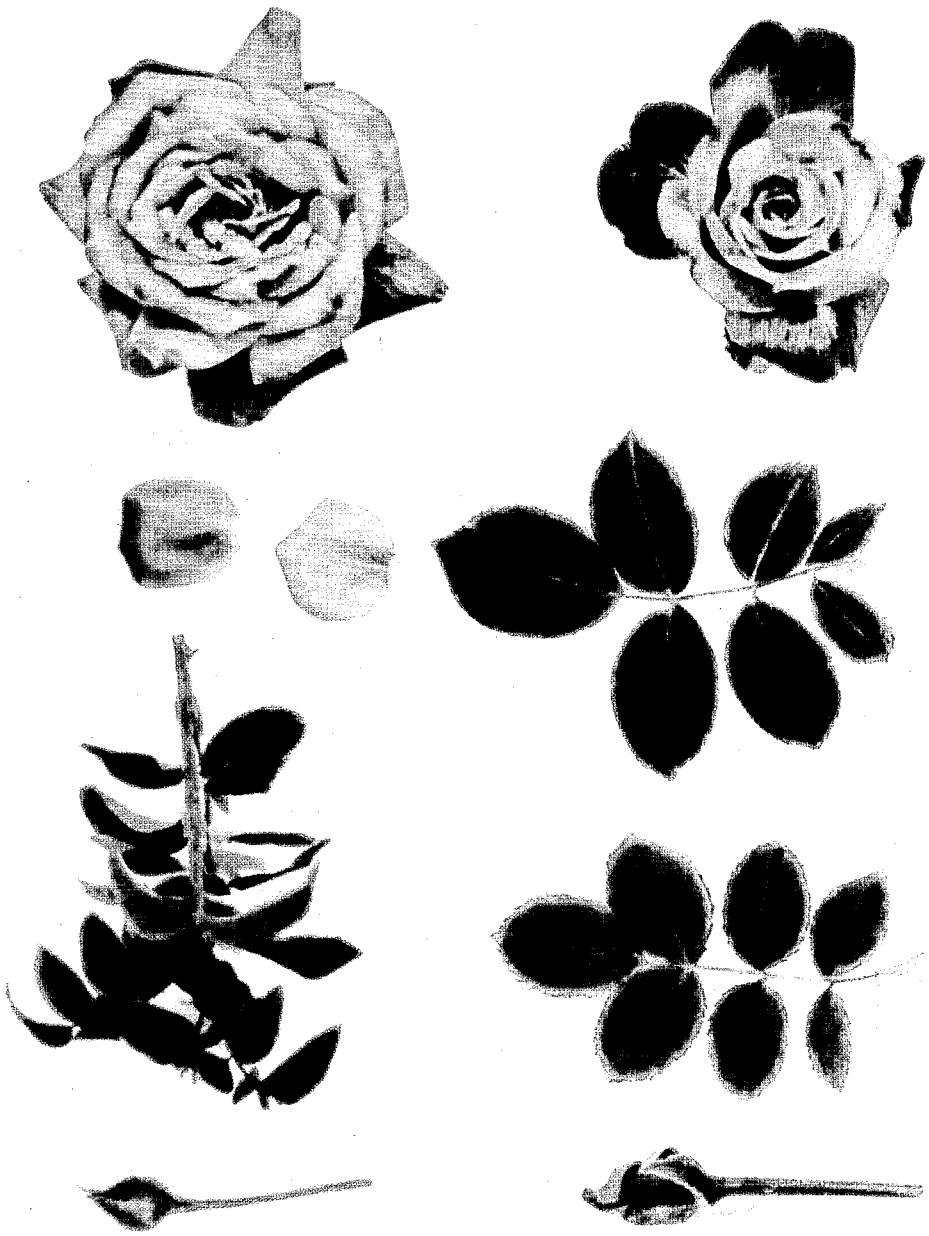
Inventor.
Alain Meilland
By: Robb & Robb
Attorneys.

United States Patent Office

Plant Pat. 2,359
Patented Feb. 4, 1964

2,359
ROSE PLANT

Alain Meilland, Alpes Maritimes, France, assignor to The Conard-Pyle Company, West Grove, Pa., a corporation of Pennsylvania Filed Feb. 5, 1963, Ser. No. 256,488
1 Claim. (Cl. Plt.—11)

The present invention relates to a new and distinct variety of rose plant of the hybrid tea class, which was originated by me by crossing the variety known as "Paris Match" (unpatented) with an unnamed and unpatented seedling derived from a cross of "Baccara" (U.S. Plant Patent No. 1,367)×"Happiness," known in France as "Rouge Meilland" (U.S. Plant Patent No. 911).

The primary objective of this breeding was to produce a new rose variety of the hybrid tea class which combines the desirable plant growth characteristics of the unnamed seedling parent with the flower characteristics of the parent variety "Paris Match." This objective was fully achieved, along with other desirable features, as evidenced by the following unique combination of characteristics which are outstanding in the new variety and which distinguish it from its parents, as well as from all other varieties of which I am aware:

(1) A vigorous and well-branched plant habit;

(2) A flower form which is distinctly superior to that of both parent varieties;

(3) A distinctive and attractive general color tonality of the flowers corresponding to Tyrian Purple, shaded with Garnet Lake, said coloration being darker and richer than the flower color of both parent varieties; and (4) A strong and rich flower fragrance.

In comparison with its parents, the new variety is better branched and more vigorous, while the flowers have greater petalage and a color tonality which is a darker red color than the parent "Paris Match," while lacking the orange undertones of the unnamed seedling parent.

Asexual reproduction of my new variety by budding, as performed in Frances, and also at West Grove, Pennsylvania, U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Horticultural Colour Chart of the Royal Horticultural Society, except where general color terms of ordinary dictionary significance are obvious:

Type: Hardy; bush; outdoor; seedling; for garden decoration.

Class: Hybrid tea.

Breeding: Seedling.

*Seed parent.*—"Paris Match."

*Pollen parent.*—An unnamed seedling of "Baccara" ×"Happiness."

Propagation: Holds its distinguishing characteristics through succeeding propagations by budding.

*Flower*

Locality where grown and observed: West Grove, Pennsylvania, U.S.A.

Flowers borne: Generally singly to stem; on medium to long and strong stems.

Quantity of bloom: Free, outdoors.

Continuity: Continuous.

Fragrance: Strong. Nature—tea.

Bud:

*Peduncle.*—Long; medium heavy; erect; rough; with medium number of brown hairs. Color—Lettuce Green, Plate 861/1, overlaid where exposed to sun with Oxblood Red, Plate 00823/3.

*Before calyx breaks.*—Size—medium large. Form—medium length; point-ovoid; with a conspicuous neck; generally without foliaceous appendages on the surface of the bud; with bristle-like foliaceous parts extending beyond the tip of the bud equal to ¼ or more of its length.

*As calyx breaks.*—Color—Ruby Red, Plate 827, with Black shadings.

*As first petal opens.*—Size—medium large. Form—medium length; ovoid. Color: outside—near Chrysanthemum Crimson, Plate 824, shading to black where first exposed to light; inside—near Chrysanthemum Crimson, Plate 824, often streaked with Pod Green, Plate 061/3.

*Opening.*—Opens up well.

Bloom:

*Size (when fully open).*—Large; from 3½ inches to 4 inches.

*Petalage.*—Double; from 35 to 42 petals; arranged regularly.

*Form.*—High-centered at first and remaining high-centered; petals being at first loosely rolled outward and remaining loosely rolled outward at maturity.

Petals:

*Texture.*—Medium thickness.

*Appearance.*—Inside—velvety. Outside—shiny.

*Shape.*—Outer petals—obovate. Intermediate petals—obovate. Inner petals—obovate; irregular.

This description of a newly opened flower was made from a rose grown outdoors during the month of September at West Grove, Pennsylvania, U.S.A.:

*Color.*—Outer petal: outside surface—Tyrian Purple, Plate 727/1, shaded with Indian Lake, Plate 826 over basal half of petal, and with point of attachment Pod Green, Plate 061/2; inside surface—near Indian Lake, Plate 826, often blotched with near Garnet Lake, Plate 828, and with point of attachment Primrose Yellow, Plate 601/2. Intermediate petal: outside surface—Tyrian Purple, Plate 727/1, grading to Tyrian Purple, Plate 727 over basal half of petal, and with point of attachment Pod Green, Plate 061/2; inside surface—Tyrian Purple, Plate 727, shading to near Cardinal Red, Plate 822/2 and then to a zone of China Rose, Plate 024 surrounding the point of attachment, with point of attachment Primrose Yellow, Plate 601/2. Inner petal: outside surface—Tyrian Purple, Plate 727, usually with a streak of Rose Pink, Plate 427/2 extending along the midrib; inside surface—Tyrian Purple, Plate 727/1 over apical margin, grading to Tyrian Purple, Plate 727 over main body of petal, with point of attachment Mimosa Yellow, Plate 602/1.

This description was made from a rose that was open for three days outdoors during the month of September at West Grove, Pennsylvania, U.S.A.:

*Color.*—Outer petal: outside surface—Tyrian Purple, Plate 727, often irregularly blotched with black and shaded with two irregular zones of Indian Lake, Plate 826 on either side of midrib over the lower half of the petal, with point of attachment Pod Green, Plate 061/2; inside surface—between Indian Lake, Plate 826 and Tyrian Purple, Plate 727, often blotched with blackened areas becoming overlaid with Indian Lake, Plate 826 toward base of petal, and with point of attachment Primrose Yellow, Plate 601/2. Inner petal: outside surface—Tyrian Purple, Plate 727/1, grading to Rose Red, Plate 724 at base of petal, with point of attachment Pod Green, Plate 061/2; inside surface—Tyrian Purple, Plate 727, margined with near Garnet Lake, Plate 828 at apex of petal, grading to Rose Red, Plate 724 over lower half of petal, and with point of attachment Primrose Yellow, Plate 601/2.

*General color effect.*—Newly opened flower—Tyrian Purple, Plate 727, shaded along margins of petals with near Garnet Lake, Plate 828. Three days open—Tyrian Purple, Plate 727, with edges of petals often margined with black where first exposed to sunlight.

*Behavior.*—Drop off cleanly; fading purple; in hot and dry weather, blackened areas of outer surfaces of outer petals become more frequent.

*Flower longevity.*—On bush in garden—4 days in September. Cut roses grown outdoors and kept at living-room temperatures—5 days in September.

*Reproductive Organs*

Stamens: Medium number; arranged irregularly about pistils.

Filaments: Most with anthers. Color—Aureolin, Plate 3/2 at base, grading to Rose Opal, Plate 022/1.

Anthers: Open at various times; medium size; occasionally an anther fused with a petaloid. Color—Chinese Yellow, Plate 606/1.

Pollen: Moderate quantity. Color—gold.

Pistils: Medium number.

Styles: Uneven; medium length; medium heaviness; bunched.

Stigma: Color—white.

Ovaries: Some protruding from receptacle.

Hips: None observed.

Sepals: Permanent; medium length; spear-shaped.

Seeds: None observed.

*Plant*

Foliage:

*Leaves.*—Compound of 5 and often 7 leaflets; normal abundance; medium large size; leathery.

*Leaflets.*—Shape—oval, with apex acute. Base—obtuse. Margin—simply serrate.

*Color.*—Mature: upper surface—Spinach Green, Plate 0960/1; under surface—Lavender Green, Plate 000761. Young: upper surface—near Maroon, Plate 1030; under surface—near Erythrite Red, Plate 0027.

*Rachis (the supporting stem of the compound leaf).*—Medium size. Upper side—grooved; hairy. Under side—sparsely prickly.

*Stipules.*—Short; narrow; with short points turning out at an angle of 45°.

*Disease resistance.*—Comparable to that of the average variety grown under the same cultural conditions at West Grove, Pennsylvania, U.S.A.

Growth:

*Habit.*—Upright; much-branched.

*Growth.*—Free.

*Canes.*—Moderately heavy.

*Main stems.*—Bright. Color—Spinach Green, Plate 0960/1. Prickles—several; hooked downward; Color—near Garnet Brown, Plate 00918/2. Hairs—none.

*Branches*—Bright. Color—Spinach Green, Plate 0960/1. Prickles—several; hooked downward; color—near Garnet Brown, Plate 00918, grading to Fern Green, Plate 0862/1 at point. Hairs—none.

*New shoots.*—Bright. Color—near Lettuce Green, Plate 861, overlaid with Oxblood Red, Plate 00823/3. Prickles—several; color—near Purple Madder, Plate 1028/1. Hairs—none.

I claim:

A new and distinct variety of rose plant of the hybrid tea class, substantially as herein shown and described, characterized particularly as to novelty by the unique combination of a vigorous and well-branched plant habit, a flower form which is distinctly superior to the parent varieties, a general color tonality of the flowers corresponding to Tyrian Purple shaded with Garnet Lake, said flower color being darker and richer than that of the parent varieties, and a strong and rich flower fragrance.

No references cited.